(12) United States Patent
Kennedy

(10) Patent No.: US 11,527,306 B2
(45) Date of Patent: Dec. 13, 2022

(54) STREAMLINED METHOD FOR ANALYTICAL VALIDATION OF BIOCHEMICALS DETECTED USING AN UNTARGETED MASS-SPECTROMETRY PLATFORM

(71) Applicant: Metabolon, Inc., Morrisville, NC (US)

(72) Inventor: Adam D. Kennedy, Durham, NC (US)

(73) Assignee: METABOLON, INC., Morrisville, NC (US)

( * ) Notice: Subject to any disclaimer, the term of this patent is extended or adjusted under 35 U.S.C. 154(b) by 294 days.

(21) Appl. No.: 16/647,883

(22) PCT Filed: Oct. 4, 2018

(86) PCT No.: PCT/US2018/054363
§ 371 (c)(1),
(2) Date: Mar. 17, 2020

(87) PCT Pub. No.: WO2019/074757
PCT Pub. Date: Apr. 18, 2019

(65) Prior Publication Data
US 2021/0233616 A1  Jul. 29, 2021

Related U.S. Application Data

(60) Provisional application No. 62/596,242, filed on Dec. 8, 2017, provisional application No. 62/570,308, filed on Oct. 10, 2017.

(51) Int. Cl.
*G16B 40/10* (2019.01)
*G16C 20/20* (2019.01)
*H01J 49/00* (2006.01)

(52) U.S. Cl.
CPC ............. *G16B 40/10* (2019.02); *G16C 20/20* (2019.02); *H01J 49/0036* (2013.01)

(58) Field of Classification Search
CPC ............ G01N 15/1459; G01N 15/1012; H01J 49/0036; G16C 20/20; G16B 40/00; G16B 40/10
See application file for complete search history.

(56) References Cited

U.S. PATENT DOCUMENTS

| | | | |
|---|---|---|---|
| 4,863,873 A | 9/1989 | Matson | |
| 5,104,639 A | 4/1992 | Matson | |
| 5,284,567 A | 2/1994 | Matson | |
| 5,290,420 A | 3/1994 | Matson | |
| 6,480,808 B1 | 11/2002 | Early et al. | |
| 2003/0167152 A1 | 9/2003 | Mark | |
| 2004/0072245 A1 | 4/2004 | Gustafsson et al. | |
| 2007/0243600 A1 | 10/2007 | Lair et al. | |
| 2011/0066385 A1* | 3/2011 | Rajwa | G01N 15/1459 702/180 |

FOREIGN PATENT DOCUMENTS

| | | |
|---|---|---|
| WO | 92/13273 A1 | 8/1992 |
| WO | 99/27361 A1 | 6/1999 |
| WO | 2015161078 A1 | 10/2015 |
| WO | 2017077401 A1 | 5/2017 |

OTHER PUBLICATIONS

ISA/US; International Search Report and Written Opinion for International Patent Application No. PCT/US18/54363 dated Nov. 23, 2018, 13 pages.
Miller, MJ et al., "Untargeted metabolomic analysis for the clinical screening of inborn errors of metabolism". Journal of Inherited Metabolic Disease, Nov. 2015; 38(6):1029-39.
CLSI. Mass Spectrometry in the Clinical Laboratory: General Principles and Guidance; Approved Guideline. CLSI document C50-A. Wayne, PA: Clinical and Laboratory Standards Institute, 2007, 84 pages.
EPO; Extended European Search Report for European Patent Application No. 18866744.8 dated May 28, 2021, 13 pages.
Dong, Zhen, et al., "A UHPLC-MS/MS method for profiling multifunctional steroids in human hair", Analytical and Bioanalytical Chemistry, vol. 409, No. 20, Jun. 20, 2017, 19 pages.
Koek, Maud M., et al., "Quantitative metabolomics based on gas chromatography mass spectrometry: status and perspectives", Metabolomics, vol. 7, No. 3, Nov. 16, 2010, 22 pages.
Jorge, Tiago F., et al., "Mass spectrometry as a quantitative tool in plant metabolomics", Royal Society of London, Philosophical Transactions. Mathematical, Physical and Engineering Sciences, vol. 374, No. 2079, Oct. 28, 2016, 26 pages.
Pereira, Helene, et al., "Development and validation of a UPLC/MS method for a nutritional metabolomic study of human plasma", Metabolomics, vol. 6, No. 2, Nov. 4, 2009, 12 pages.
CNIPA; Office Action for Chinese Patent Application No. 201880065418.7 dated Jun. 28, 2021, 14 pages.
CNIPA; Rejection Decision for Chinese Patent Application No. 201880065418.7 dated May 25, 2022, 10 pages.
NIPO; International Preliminary Report on Patentability for International Patent Application No. PCT/US2018/054363 dated Apr. 23, 2020, 12 pages.
CNIPA; Office Action for Chinese Patent Application No. 201880065418.7 dated Jan. 5, 2022, 12 pages.
JPO; Office Action for Japanese Patent Application No. 2020-520283 dated Aug. 4, 2022, 7 pages.

* cited by examiner

*Primary Examiner* — David E Smith
*Assistant Examiner* — Hsien C Tsai
(74) *Attorney, Agent, or Firm* — NK Patent Law

(57) ABSTRACT

A method of assessing the analytical performance of a biochemical measured using a multi-analyte assay is described. The method includes analytically validating a measurement of the level of a first biochemical in a sample, wherein the first biochemical has been previously analytically validated for three or more analytical validation conditions; measuring the level of a second biochemical in a sample, wherein the second biochemical is structurally or biochemically related to the first biochemical; and comparing validation parameters of the first biochemical with validation parameters of the second biochemical to determine whether the performance of the second biochemical is acceptable based on the comparison results.

19 Claims, No Drawings

STREAMLINED METHOD FOR ANALYTICAL VALIDATION OF BIOCHEMICALS DETECTED USING AN UNTARGETED MASS-SPECTROMETRY PLATFORM

CROSS-REFERENCE TO RELATED APPLICATIONS

This application is a U.S. National Stage application of International Patent Application No. PCT/US18/54363, filed on Oct. 4, 2018, which claims the benefit of U.S. Provisional Patent Application No. 62/596,242, filed on Dec. 8, 2017, and also claims the benefit of U.S. Provisional Patent Application No. 62/570,308, filed on Oct. 10, 2017.

BACKGROUND

Metabolomic profiling (global biochemical profiling) is a large scale, semi-quantitative method that examines perturbations related to biochemical abnormalities such as those in amino acid, carbohydrate, organic acid, lipid, and nucleotide metabolism. The test analyzes thousands of compounds simultaneously using a combination of chromatography and mass spectrometry (e.g., GC-MS and LC-MS/MS) technologies. Metabolomic profiling can be used as a screening tool for individuals who have, for example, an undifferentiated phenotype or as supportive evidence in individuals with equivocal mutations in genes related to metabolic processes.

For example, biochemical screening studies in the area of inborn errors of metabolism (IEM) have shown the clinical significance and utility of the metabolomic profiling approach (Miller, M J et al. J Inherit Metab Dis. 2015 November; 38(6):1029-39). The screening of the human metabolome in sample types such as plasma, serum, urine and cerebrospinal fluid has revealed informative and novel metabolic signatures as compared to the limited biochemical analysis provided by clinical diagnostic kits. The ability to use a metabolomic profiling approach to generate biochemical phenotypes provides an additional analytical tool to detect abnormal levels of metabolite production that can be used in combination with targeted, quantitative biochemical assays. Importantly, global biochemical profiling identifies and measures the levels of biochemicals not currently monitored in clinical diagnostic kits, which has underscored the utility of global metabolomic profiling as a tool for monitoring a variety of clinically relevant biochemicals.

Before a test or assay can be used in a clinical setting, certain regulatory requirements must be fulfilled. In addition to clinical validation and clinical utility, analytical validation must be demonstrated. Traditional approaches for validating a biochemical for use in clinical applications require full analytical validation of each biochemical by assessing numerous conditions including, for example single-day precision (intra-day precision), multi-day precision (inter-day precision), limit of detection (LOD), linearity, stability, carryover, matrix effect/biochemical recovery, interference, and comparison to currently used standard clinical assays by correlation analysis.

Global metabolomic profiling has been experimentally demonstrated to be a useful method for assessing health and diagnosis of disease. However, the process of analytically validating all of the biochemicals in a metabolomic profile for all validation conditions for the analytical validation of biochemical analytes is extremely time and resource intensive, which limits the use of the metabolomic profiling method in the clinical setting due to the extensive analytical parameters that must be assessed and satisfied to fulfill regulatory requirements for analytical validation. Methods for quantitation allowing for measurement of the level of one compound based on the level of an internal standard for a compound with similar chemical characteristics to the first compound have been suggested (CLSI. Mass Spectrometry in the Clinical Laboratory: General Principles and Guidance; Approved Guideline. CLSI document C50-A. Wayne, Pa.: Clinical and Laboratory Standards Institute; 2007). However, that approach requires calibration standards and internal standards to accurately quantify the compounds. As such, its application to analytical validation of a global metabolomic profile is limited by the number of internal standards that can be analyzed simultaneously with the vast number of compounds measured using the metabolomic technology.

SUMMARY

Analytical validation of biochemical assays to fully meet defined validation conditions is routinely performed on quantitative assays of single analytes or multi-analyte panels consisting of a limited number of analytes. Typically, the multi-analyte panels consist of fewer than 50 analytes. However, this full analytical validation approach is not feasible for semi-quantitative, multi-analyte panels comprised of tens to hundreds or thousands of analytes. To enable the utility of semi-quantitative global metabolomics assays for assessing human health, a streamlined method to analytically validate the large number of analytes measured in these assays without performing full analytical validation on each analyte, is needed.

In the methods described, the analytical performance of a biochemical in an assay is assessed and validated using a streamlined set of analytical validation conditions. In some embodiments, the biochemical is structurally related to another metabolite that has been fully analytically validated. In some embodiments, the biochemical is biochemically related to another metabolite that has been fully analytically validated.

In an aspect of the present invention, a method of assessing the analytical performance of a biochemical measured using a multi-analyte assay comprises analytically validating the measurements of the level of a first biochemical in a sample, wherein the first biochemical has been analytically validated (i.e., meets or surpasses the values established for the acceptance criteria, the "reference values") for a plurality of analytical validation conditions selected from the list comprising: Intra-day Precision, Inter-day Precision, Linearity, Limit of Detection (or Limit of Quantitation), Matrix effect, Exogenous Interference, Recovery, Stability, Carryover, and Comparison to (i.e. correlation with) measurements obtained using standard clinical assays; measuring the level of a second biochemical in a sample, wherein the second biochemical is structurally or biochemically related to the first biochemical; selecting one or more of the analytical validation conditions; determining or calculating performance values for the selected one or more analytical validation conditions for the second biochemical based on the measured level of the second biochemical; comparing the determined or calculated performance values of the analytical validation conditions for the first biochemical with the determined or calculated performance values of the analytical validation condition for the second biochemical; determining the performance of the second biochemical to be acceptable if the calculated performance values of the second biochemical meets an acceptance criterion for the analytical validation condition, and determining the analytical performance of the second biochemical to be unacceptable if the calculated performance value(s) of the second biochemical does not meet the acceptance criterion for the analytical validation condition.

In an embodiment of the first aspect, the analytical performance of the second biochemical is determined to be acceptable if the calculated performance value(s) of the second biochemical are within 50% of the values for the first biochemical; and the analytical performance of the second biochemical is determined to be unacceptable if the calculated performance value(s) of the second biochemical are not within 50% of the first biochemical. In another embodiment the analytical performance of the second biochemical is determined to be acceptable if the calculated performance value(s) of the second biochemical are within 70% of the value(s) for the first biochemical; and the analytical performance of the second biochemical is determined to be unacceptable if the calculated performance value(s) of the second biochemical are not within 70% of the value(s) of the first biochemical.

In some embodiments the first biochemical is analytically validated for two or more analytical validation conditions. In other embodiments, the first biochemical is analytically validated for three or more, four or more, five or more, six or more, seven or more, eight or more, nine or more, or ten or more, or all of the analytical validation conditions.

In yet another embodiment, two analytical validation conditions are selected for the second biochemical. In a feature of this embodiment, the two conditions may be intra-day (single day) precision and inter-day (multi-day) precision. In another aspect of this embodiment the performance values calculated for the performance acceptance criteria comprise % fill and % CV.

In a second aspect of the invention, a method of assessing the performance of a biochemical measured using a multi-analyte assay is provided. The method comprises: measuring the level of a biochemical in a sample, wherein the biochemical is structurally or biochemically related to one or more biochemicals that has been fully analytically validated (i.e., meets acceptance criteria for all of the analytical validation conditions); selecting one or more analytical validation conditions selected from the group consisting of single-day precision (intra-day precision), multi-day precision (inter-day precision), limit of detection or quantitation (LOD, LOQ), linearity, stability, carryover, matrix effect, biochemical recovery, interference, and correlation with standard clinical assays; calculating a performance value(s) for the selected one or more analytical validation conditions for the biochemical based on the measured level of the biochemical in the sample; comparing the calculated performance value(s) for the one or more analytical validation conditions for the biochemical to an acceptance criterion for the one or more analytical validation conditions; and determining the analytical performance of the biochemical to be acceptable if it meets the acceptance criterion or unacceptable if it does not meet the acceptance criterion for the corresponding analytical validation condition.

In a third aspect of the present invention, a method of assessing the performance of a biochemical measured using an assay comprises: measuring the level of a biochemical in a sample, wherein the biochemical is structurally or biochemically related to one or more biochemicals listed in Table 1 or Table 2; selecting one or more analytical validation conditions from the group comprising single-day precision (intra-day precision), multi-day precision (inter-day precision), limit of detection or quantitation (LOD, LOQ), linearity, stability, carryover, matrix effect, biochemical recovery, interference, and comparison to (correlation with) standard clinical assays, determining or calculating performance values for the selected one or more analytical validation conditions for the biochemical based on the measured level of the biochemical in the sample, comparing the calculated performance values of the one or more analytical validation conditions for the biochemical with reference values for the acceptance criteria for the one or more analytical validation conditions, determining the analytical performance of the biochemical to be acceptable if the analytical performance value meets or exceeds the reference value for the acceptance criterion or unacceptable if it does not meet the acceptance criterion reference value for the corresponding analytical validation condition.

In an embodiment of the aspects, the analytical performance of at least 50 biochemicals is assessed in a single multi-analyte assay. In another embodiment, the analytical performance of at least 100 biochemicals is assessed in a single multi-analyte assay. In yet another embodiment, the analytical performance of at least 150 biochemicals is assessed in a single multi-analyte assay. In a further embodiment, the analytical performance of at least 200 biochemicals is assessed in a single multi-analyte assay. In an additional embodiment, the analytical performance of at least 500 biochemicals is assessed in a single multi-analyte assay. In a still further embodiment, the analytical performance of at least 1000 biochemicals is assessed in a single multi-analyte assay.

In an embodiment of the aspects, the multi-analyte assay is comprised of at least 50 biochemicals. In another embodiment, the multi-analyte assay is comprised of at least 100 biochemicals. In yet another embodiment, the multi-analyte assay is comprised of at least 150 biochemicals. In a further embodiment, the multi-analyte assay is comprised of at least 200 biochemicals. In an additional embodiment, the multi-analyte assay is comprised of at least 500 biochemicals. In a still further embodiment, the multi-analyte assay is comprised of at least 1000 biochemicals.

In another embodiment, the performance acceptance criteria for an analytical validation condition are selected from the group comprising, correlation analysis ($R^2$), % fill, % Systematic Error (SE), % Bias, % Difference, and % Coefficient of Variation (CV). In a feature of this embodiment, when the analytical validation conditions is % fill, a performance value of at least 80% meets acceptance criterion.

In a feature of the aspects, one of the one or more selected analytical validation conditions is intra-day precision. In another feature of the aspects, one of the one or more selected analytical validation conditions is inter-day precision. In these feature, a performance value of 30% CV or less meets acceptance criterion. Further in these feature, a performance value of 25% CV or less meets acceptance criterion.

In an embodiment of the second and third aspects, two analytical validation conditions are selected. In a feature of this embodiment, the two analytical validation conditions are intra-day (single day) precision and inter-day (multi-day) precision. In another feature of this embodiment, the analytical validation condition is intra-day precision, a calculated value of 30% CV or less for the biochemical is determined to be acceptable performance. In a further feature, the analytical validation condition is intra-day precision and a calculated value of 25% CV or less for the biochemical is determined to be acceptable performance. In yet another feature, the analytical validation condition is inter-day precision, a calculated value of 30% CV or less for the biochemical is determined to be acceptable performance. In a still further feature, the analytical validation condition is inter-day precision, a calculated value of 25% CV or less for the biochemical is determined to be acceptable performance.

In a feature of the aspects, the assay comprises mass spectrometry. In a further feature, the assay comprises liquid chromatography and mass spectrometry. In yet another feature, the sample comprises a plasma, serum, urine, or CSF sample.

Definitions

"Biochemical", "compound", "small molecule", "metabolite" "analyte" as used herein means organic and inorganic molecules that are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates, which can be metabolized further or used to generate large molecules, called macromolecules. The term "small molecules" includes signaling molecules and intermediates in the chemical reactions that transform energy derived from food into usable forms. Non-limiting examples of small molecules include sugars, fatty acids, amino acids, nucleotides, intermediates formed during cellular processes, and other small molecules found within the cell.

"Pathway" is a term commonly used to define a series of steps or reactions that are linked to one another. For example, a biochemical pathway whereby the product of one reaction is a substrate for a subsequent reaction. Biochemical reactions are not necessarily linear. Rather, the term biochemical pathway is understood to include networks of inter-related biochemical reactions involved in metabolism, including biosynthetic and catabolic reactions. "Pathway" without a modifier can refer to a "super-pathway" and/or to a "subpathway." "Super-pathway" refers to broad categories of metabolism. "Subpathway" refers to any subset of a broader pathway. For example, glutamate metabolism is a subpathway of the amino acid metabolism biochemical super-pathway. Metabolites in the same biochemical pathway are referred to as "biochemically related".

"Global metabolomic profiling" or "global biochemical profiling" refers to a method of assaying the level of biochemicals in a sample. The method measures the level of hundreds of biochemicals in a sample thereby providing a biochemical screen. The method may also be generally referred to as an "assay".

"Test sample" means the sample to be analyzed.

"Reference sample" means a sample used for determining a standard range for a level of small molecules. "Reference sample" may refer to an individual sample. The sample may be from an individual reference subject (e.g., a normal (healthy) reference subject or a disease reference subject), who may be selected to closely resemble the test subject by age and gender. "Reference sample" may also refer to a sample including pooled aliquots from reference samples for individual reference subjects.

"Accuracy" refers to the ability of a measurement to match the actual biochemical identification and relative level of the quantity being measured.

"Precision" refers to the ability of a measurement to be consistently reproduced.

"Analytical validation" refers to the evaluation process that an analytical procedure or assay undergoes to demonstrate that it is suitable for its intended purpose by meeting or surpassing acceptance criteria for performance characteristics, such as, for example, single-day precision (intra-day precision), multi-day precision (inter-day precision), limit of detection or quantitation (LOD, LOQ), linearity, stability, carryover, matrix effect, biochemical recovery, interference, and correlation with standard clinical assays. The performance characteristics are also referred to herein as performance conditions. The acceptance criteria are associated with target values and acceptance limits around a target value. The reference value for an acceptance criterion is the range determined by the acceptance limit around the acceptance target value. For example, the target value may be 12, with a standard deviation (SD) of 0.5 and an acceptance limit of +/−1.5. In this example, the reference value would range from 10.5 to 13.5 and values within that range would meet the acceptance criterion.

"Coefficient of Variance" or "CV" refers to the ratio of the standard deviation of a biochemical as measured in a plurality of samples to the mean of the biochemical in the plurality of samples. The ratio is typically presented as a percentage (% CV).

"Bias" refers to the difference between the expectation of the test results and an accepted reference value (note that in the case of interference testing, the "accepted value" would be the result from the same measurement procedure in the absence of the interference).

"Limit of Detection" or "LOD" or "Limit of Quantitation" or "LOQ" as used herein refers to the lowest amount of analyte in a sample that can be detected with a stated probability, although not necessarily quantified as an exact value. This is also called the "minimum detectable concentration", and sometimes is used to indicate the functional sensitivity of the test. The terms may be used herein interchangeably.

"Recovery" refers to the amount of substance present in a sample that can be detected by the analytical system. Usually this is referred to as the percent recovery. A system where there is 100% recovery is perfectly accurate.

DETAILED DESCRIPTION

Described herein are methods for performing streamlined analytical validation of a plurality of biochemicals. The methods comprise assessing the performance of a biochemical using a multi-analyte assay (e.g., global metabolomics assays). In this global metabolomics approach, a selected subset of biochemicals, representing diverse biochemical pathways, are analytically validated for the analytical validation conditions required by regulatory agencies such as, for example the US Food and Drug Administration or the European Medicines Agency (EMA), (i.e., fully analytically validated). Using a streamlined set of analytical validation conditions, the performance of other biochemically- or structurally-related biochemicals that are not directly tested in the full analytical validation protocols can be assessed and analytically validated. Generally, the biochemicals assessed using the streamlined performance conditions are structurally or biochemically related to one or more biochemicals that were fully analytically validated.

The global metabolomics profiling assay method described herein identifies small molecules between about 50 Daltons (Da) and about 1,500 Da in molecular weight.

The identities of the small molecules are determined by comparing them to a biochemical library. The library (currently containing over 4,000 biochemicals) was built using purified authentic chemical standards for each compound analyzed using LC-MS/MS methods. The library includes compound-specific features of each molecule, which are used to identify compounds in future samples. The library contains, for each molecule, the molecular weight/mass and analytical characteristics (features), including but not limited to, for example, information regarding adducts, in source fragmentation, polymerization, chromatographic retention time, and mass spectral fragmentation patterns.

The biochemicals may be grouped into super pathways including, for example, Amino Acid; Peptide; Carbohydrate; Energy; Lipid; Complex Lipids; Nucleotide; Cofactors and Vitamins; and Xenobiotics. Biochemical may also be grouped into one or more biochemical subpathways, including, for example: Glycine, Serine and Threonine Metabolism; Alanine and Aspartate Metabolism; Glutamate Metabolism; Histidine Metabolism; Lysine Metabolism; Phenylalanine and Tyrosine Metabolism; Tryptophan Metabolism; Leucine, Isoleucine and Valine Metabolism; Methionine, Cysteine, SAM and Taurine Metabolism; Urea cycle; Arginine and Proline Metabolism; Creatine Metabolism; Polyamine Metabolism; Guanidino and Acetamido Metabolism; Glutathione Metabolism; Felinine Metabolism; Gamma-glutamyl Amino Acid; Dipeptide Derivative; Dipeptide; Polypeptide; Fibrinogen Cleavage Peptide; Glycolysis, Gluconeogenesis, and Pyruvate Metabolism; Glycolysis, Gluconeogenesis, and Pyruvate Metabolism; Pentose Phosphate Pathway; Pentose Metabolism; Glycogen Metabolism; Disaccharides and Oligosaccharides; Fructose, Mannose and Galactose Metabolism; Nucleotide Sugar; Aminosugar Metabolism; Advanced Glycation End-product; TCA Cycle; Oxidative Phosphorylation; Short Chain Fatty Acid; Medium Chain Fatty Acid; Long Chain Fatty Acid; Polyunsaturated Fatty Acid (n3 and n6); Quantitative Free Fatty Acid; Fatty Acid, Branched; Fatty Acid, Dicarboxylate; Fatty Acid, Methyl Ester; Fatty Acid, Ester; Fatty Acid, Amide; Fatty Acid, Keto; Fatty Alcohol, Long Chain; Fatty Acid Synthesis; Fatty Acid Metabolism; Fatty Acid Metabolism (also BCAA Metabolism); Fatty Acid Metabolism(Acyl Glycine); Fatty Acid Metabolism(Acyl Carnitine); Carnitine Metabolism; Ketone Bodies; Neurotransmitter; Fatty Acid, Monohydroxy; Fatty Acid, Dihydroxy; Fatty Acid, Oxidized; Eicosanoid; Endocannabinoid; Inositol Metabolism; Phospholipid Metabolism; Lysolipid; Glycerolipid Metabolism; Monoacylglycerol; Diacylglycerol; Sphingolipid Metabolism; Mevalonate Metabolism; Sterol; Steroid; Primary Bile Acid Metabolism; Secondary Bile Acid Metabolism; Diacylglycerol; Triacylglycerol; Lysophosphatidylcholine; Phosphatidylcholine; Phosphatidylethanolamine; Phosphatidylserine; Sphingomyelin; Sphingolipid Metabolism; Cardiolipin; Cholesterol Ester; Phospholipids; Purine Metabolism, (Hypo)Xanthine/Inosine containing; Purine Metabolism, Adenine containing; Purine Metabolism, Guanine containing; Pyrimidine Metabolism, Orotate containing; Pyrimidine Metabolism, Uracil containing; Pyrimidine Metabolism, Cytidine containing; Pyrimidine Metabolism, Thymine containing; Purine and Pyrimidine Metabolism; Nicotinate and Nicotinamide Metabolism; Riboflavin Metabolism; Pantothenate and CoA Metabolism; Ascorbate and Aldarate Metabolism; Tocopherol Metabolism; Biotin Metabolism; Folate Metabolism; Tetrahydrobiopterin Metabolism; Pterin Metabolism; Hemoglobin and Porphyrin Metabolism; Lipoate Metabolism; Thiamine Metabolism; Vitamin K Metabolism; Vitamin A Metabolism; Vitamin B12 Metabolism; Vitamin B6 Metabolism; Benzoate Metabolism; Xanthine Metabolism; Tobacco Metabolite; Food Component/Plant; Bacterial; Drug; Phthalate; and Chemical.

In exemplary embodiments of the method, samples are analyzed (referred to herein as "run") on a mass spectrometry instrument system (referred to herein as a platform) using, for example, LC-MS/MS assay methods. Biochemicals in the samples are identified by comparison to the biochemical library of authentic standards. Identification is made based on features including, for example, retention time, retention index, accurate mass, and biochemical fragmentation patterns. Signal intensity of a selected ion fragment (quant ion) for each of the identified biochemicals in a test sample can be compared to, for example, those obtained from other test samples, or one or more reference samples. This approach achieves relative quantitation for each biochemical for a sample, or a group of samples. The samples may be test samples or reference samples. Relative biochemical quantitation may be used to compare individual samples or groups of samples based on the levels of biochemicals and/or the levels of biochemicals in biochemical pathways. Relative biochemical quantitation is useful to compare the same molecule between samples.

Biochemicals measured in an assay that is intended for clinical use (e.g., as a laboratory developed test, LDT) must be analytically validated to satisfy regulatory requirements.

Performance of a biochemical for analytical validation can be assessed using a number of analytical validation conditions, including, but not limited to single-day precision (intra-day precision), multi-day precision (inter-day precision), limit of detection (LOD), linearity, stability, carryover, matrix effect, biochemical recovery, interference, and/or comparison to/correlation with standard clinical assays. A biochemical is determined to be analytically validated if the performance values for one or more analytical validation conditions meet or exceed the acceptance criterion set for the condition (i.e., the performance value is within the reference value range). Non-limiting, exemplary acceptable performance values for performance acceptance criteria may include: % fill>80%; % CV<35%; $R^2$>0.8. Furthermore, the conditions may be assessed on multiple instrument systems (i.e., platforms) to assess inter-platform precision to demonstrate consistency and robustness of the validation analysis.

In a metabolomic profiling assay, hundreds of biochemicals are measured. Fully analytically validating all of these biochemicals is impractical due to resource requirements and time intensive. Methods to fully analytically validate a subset of biochemicals using multiple validation conditions is described herein. The analytical validation conditions and acceptance criteria necessary for analytical validation will depend on how the assay is being used. One of ordinary skill in the art will understand and appreciate the conditions and acceptance criteria needed based on assay end use. Biochemicals that meet the analytical validation criteria for the assessed analytical validation conditions necessary to fulfill regulatory requirements are determined to be, and are referred to as, "fully analytically validated", and thus can be used to analytically validate structurally or biochemically related biochemicals using a streamlined analytical validation approach.

In one embodiment, the acceptance criterion for intra-day precision and inter-day precision for a biochemical may be based on the number of samples in which the biochemical is detected ("% Fill"). In one example, a biochemical is considered to meet the acceptance criterion for intra-day precision or inter-day precision if the biochemical is detected in at least 80% of samples. In another example, a biochemical is considered to meet acceptance for intra-day precision or inter-day precision if the biochemical is detected in 100% of samples.

In another embodiment, the acceptance criterion for intra-day precision, inter-day precision and inter-platform precision for a biochemical may be based on coefficient of variance (CV). For example, a biochemical is considered to meet the acceptance criterion for intra-day precision, inter-day precision or inter-platform precision if the CV of the biochemical is less than 40%. In other examples, a biochemical is considered to meet the acceptance criterion for intra-day precision, inter-day precision or inter-platform precision if the CV of the biochemical is less than 35%, less than 30%, less than 25%, or less than 20%.

EXAMPLES

I. General Methods.

Generation of the small molecule profile of a sample requires analysis of its constituent biochemical small molecules. The analysis may include extracting at least some of the plurality of small molecules from the sample. The analysis may be conducted using one or more different analytical techniques known in the art, for example, liquid chromatography (LC), high performance liquid chromatography (HPLC) (see Kristal, et al. Anal. Biochem. 263:18-25 (1998)), gas chromatography (GC), thin layer chromatography (TLC), electrochemical separation techniques (see, WO 99/27361, WO 92/13273, U.S. Pat. Nos. 5,290,420, 5,284,567, 5,104,639, 4,863,873, and RE32,920), refractive index spectroscopy (RI), ultra-violet spectroscopy (UV), fluorescent analysis, radiochemical analysis, near-infrared spectroscopy (Near-IR), nuclear magnetic resonance spectroscopy (NMR), light scattering analysis (LS), mass spectrometry (MS), tandem mass spectrometry (MS/MS2), and combined methods such as gas-chromatography/mass spectrometry (GC-MS), liquid chromatography/mass spectrometry (LC-MS), ultrahigh performance liquid chromatography/tandem mass spectrometry (UHLC/MS/MS2) or gas-chromatography/tandem mass spectrometry (GC/MS/MS2).

The global biochemical profiling method may consist of one or more assays, including, for example, liquid chromatography (LC), gas chromatography (GC), mass spectrometry (MS), or a combination thereof. The assays may include, for example: LC Positive Ion Polar UHPLC-RP (Reverse Phase)/MS/MSn; LC Positive Ion Lipid UHPLC-RP/MS/MSn; LC Negative Ion UHPLC-RP/MS/MSn; LC Negative Ion UHPLC-HILIC (Hydrophilic Interaction Liquid Chromatography)/MS/MSn, GC-MS, or a combination thereof.

The biochemicals may be grouped into biochemical pathways (super pathways and sub-pathways). Biochemicals in the same pathway typically have similar chemical structures and are considered structurally related. Biochemicals with similar chemical structures usually have similar performance in assays. Performance was assessed for selected biochemicals (Tables 1 and 2) using each of the following conditions: single-day precision (intra-day precision), multi-day precision (inter-day precision), limit of detection (LOD), linearity, stability, carryover, matrix effect, biochemical recovery, interference, and correlation with standard clinical assays. A set of streamlined conditions was used to assess the performance of additional biochemicals, which enabled the performance of over 4,000 biochemicals to be assessed in a fraction of the time at a fraction of the cost of the full assessment.

A. Global Biochemical Profiling.

In the exemplary embodiment described herein, the global biochemical profiling method included four separate liquid chromatography (LC) mass spectrometry (MS) methods: LC Positive Ion Polar UHPLC-RP (Reverse Phase)/MS/MS″, LC Positive Ion Lipid UHPLC-RP/MS/MS″, LC Negative Ion UHPLC-RP/MS/MS″ and LC Negative Ion UHPLC-HILIC (Hydrophilic Interaction Liquid Chromatography)/MS/MS″.

B. UPLC Method.

Samples were extracted and reconstituted in solvents containing internal standards. All reconstituted aliquots analyzed by LC-MS were separated using a Waters Acquity UPLC (Waters Corp., Milford, Mass.). The aliquots reconstituted in 0.1% formic acid used mobile phase solvents consisting of 0.1% formic acid in water (A) and 0.1% formic acid in methanol (B). Aliquots reconstituted in 6.5 mM ammonium bicarbonate used mobile phase solvents consisting of 6.5 mM ammonium bicarbonate in water, pH 8 (A) and 6.5 mM ammonium bicarbonate in methanol and water. The gradient profile utilized for both the formic acid reconstituted extracts and the ammonium bicarbonate reconstituted extracts was carried out with initial conditions of 0.5% B and 350 µL/min flow rate. The total run time was less than 6 minutes. The flow rate was. The sample injection volume was 5 µL, and 2× needle loop overfill was used. Liquid chromatography separations were made at 40° C. on separate acid or base-dedicated 2.1 mm×100 mm Waters BEH C18 1.7 µm particle size columns.

C. UPLC-MS Methods.

An OrbitrapElite (OrbiElite Thermo Scientific, Waltham, Mass.) mass spectrometer was used. The OrbiElite mass spectrometers utilized a HESI-II source with sheath gas set to 80, auxiliary gas at 12, and voltage set to 4.2 kV for positive mode. Settings for negative mode had sheath gas at 75, auxiliary gas at 15 and voltage was set to 2.75 kV. The source heater temperature for both modes was 430° C. and the capillary temperature was 350° C. The mass range was 99-1000 m/z with a scan speed of 4.6 total scans per second also alternating one full scan and one MS/MS scan and the resolution was set to 30,000. The Fourier Transform Mass Spectroscopy (FTMS) full scan automatic gain control (AGC) target was set to $5 \times 10^5$ with a cutoff time of 500 ms. The AGC target for the ion trap MS/MS was $3 \times 10^3$ with a maximum fill time of 100 ms. Normalized collision energy for positive mode was set to 32 arbitrary units and negative mode was set to 30. Activation Q was 0.35 and activation time was 30 ms, again with a 3 m/z isolation mass window. The dynamic exclusion setting with 3.5 second duration was enabled. Calibration was performed weekly using an infusion of Pierce™ LTQ Velos Electrospray Ionization (ESI) Positive Ion Calibration Solution or Pierce™ ESI Negative Ion Calibration Solution.

D. Data Processing and Analysis.

For each biological matrix data set on each instrument, relative standard deviations (RSDs) of peak area were calculated for each internal standard to confirm extraction efficiency, instrument performance, column integrity, chromatography, and mass calibration. Several of these internal standards serve as retention index (RI) markers and were checked for retention time and alignment. Internal standards are used for QC purposes and are not used for quantitation of biochemical in the assay(s). Modified versions of the software accompanying the UPLC-MS system were used for peak detection and integration. The output from this processing generated a list of m/z ratios, retention times and area under the curve values. Software specified criteria for peak detection including thresholds for signal to noise ratio, height and width.

The biological data sets, including QC samples, were chromatographically aligned based on a retention index that utilizes internal standards assigned a fixed RI value. The RI of the experimental peak was determined by assuming a linear fit between flanking RI markers whose values do not change. The benefit of the RI is that it corrects for retention time drifts that were caused by systematic errors such as sample pH and column age. Each biochemical's RI was designated based on the elution relationship with its two lateral retention markers. Integrated, aligned peaks were matched against a chemical library of authentic standards and routinely detected unknown biochemicals, which was specific to the data collection method employed. Matches were based on retention index values and experimental precursor mass match to the library authentic standard. The experimental MS/MS was compared to the library spectra for the authentic standard and assigned forward and reverse scores. A perfect forward score indicated that all ions in the experimental spectra were found in the library for the authentic standard at the correct ratios and a perfect reverse score indicated that all authentic standard library ions were present in the experimental spectra and at correct ratios. The forward and reverse scores were compared and a MS/MS fragmentation spectral score was given for the proposed match.

Further details regarding a chemical library, a method for matching integrated aligned peaks for identification of named compounds and routinely detected unknown compounds, and computer-readable code for identifying small molecules in a sample may be found in U.S. Pat. No. 7,561,975, which is incorporated by reference herein in its entirety.

Example 1

Full Analytical Validation of Representative Metabolites

The analytical performance of a representative set of metabolites was assessed and fully validated using currently accepted or required conventional analytical validation techniques. Ten (10) analytical validation conditions were assessed: single-day precision (intra-day precision), multi-day precision (inter-day precision), and limit of detection/quantitation (LOD/LOQ), linearity, stability, carryover, matrix effect, biochemical recovery, interference, and correlation with standard clinical assays. Performance values were calculated for each of the analytical validation conditions for each biochemical assessed. The analytical validation and performance assessment were implemented on plasma, serum, urine, and CSF samples using four independent LC-MS/MS instrument systems, with each system referred to herein as a platform, (i.e., Platform Q, R, S and T). The analytical performance of 276 metabolites in plasma and serum samples and 176 metabolites in urine and CSF samples was assessed and fully analytically validated according to currently accepted practices and criteria as described below.

Intra-day Precision: Two independent test samples, Test Sample 1 and Test Sample 2, were used to evaluate intra-day precision. Each test sample was created by pooling six (6) different EDTA plasma samples from healthy adult volunteers (i.e., six healthy adult plasma samples were pooled to create Test Sample 1 and six healthy adult plasma samples, different from the samples used to create Test Sample 1, were pooled to create Test Sample 2). Certain metabolites were only seen in diseased patient samples and not in samples from healthy individuals; these biochemicals are designated as rare metabolites. Since these rare metabolites were absent in Test Sample 1 and Test Sample 2, these metabolites were spiked into the pooled test samples. The test samples were analyzed with 5 technical replicates for each test sample across 5 days on each of 4 LC-MS/MS platforms (Q, R, S, and T) to determine intra-day precision based upon the % CV. The % CV of the raw counts was determined for each of the metabolites listed in Tables 1 & 2 in each technical replicate sample across all 4 platforms. Optimal Intra-day Precision is % CV< or =25 and metabolites with % CV< or =25 meet the % CV acceptance criterion; however, metabolites with a 25-30% CV meet the acceptance criterion for % CV provided that no more than 3 samples have CVs in this range; metabolites with a 30-40% CV meet acceptance criterion for % CV provided that no more than 1 sample has a % CV in this range; metabolites with >40% CV intra-day precision analysis are not precise and do not meet the acceptance criterion.

Inter-day Precision: Two unique test samples were analyzed with 5 technical replicates for each test sample across 5 days to determine intra-day precision. Pooled reference samples were included for use for normalization across days (day 1-5). Nine pools of reference samples were analyzed with each sample batch and alongside the replicate test samples. The performance value for inter-day precision was calculated using % CV. The % CV for each of the biochemicals in Tables 1 & 2 was determined using the mean raw counts for each sample, normalized (i.e., divided by) against the mean raw counts of the 9 pooled reference samples. Optimal Inter-day Precision is < or =25% CV and metabolites with % CV< or =25 meet the % CV acceptance criterion; however, metabolites with a 25-35% CV for one replicate meet the acceptance criterion for % CV provided that all of the other replicates are <25% CV.

Linearity: To assess linearity, the biochemicals listed in Tables 1 and 2 were spiked into solvent at amounts covering 6 orders of magnitude and then extracted. Samples were run in triplicate on each of the 4 LC-MS/MS analytical platforms. Each biochemical was analyzed in a 6-step serial dilution series with the following concentrations: 0.0404 ng/mL, 0.482 ng/mL, 5.79 ng/mL, 69.4 ng/mL, 833 ng/mL, and 10,000 ng/mL. The mean signal intensities for each biochemical in the triplicate sample analysis, at each dilution, was graphed versus the known concentration of the biochemical. Only data points at or above the limit of detection were included in the linearity calculations. The dilution series involved six steps of 12-fold dilutions. The experiment was performed on each of the four analytical platforms. The full standard curve, including the minimum and maximum concentrations of the linear range, was calculated for each biochemical in Tables 1 and 2 for each platform, and Linearity Plots were generated. The performance value for linearity was calculated using $R^2$ and systematic error (% SE). The calculated performance value was then compared to the linearity acceptance criterion to determine if the biochemical meets or surpasses the acceptance criterion for linearity. The acceptance criteria for analytical validation for linearity was as follows: the $R^2$ value for the biochemical must be >0.95 and the % Systematic Error (SE) should be within 20% at the lowest concentration point, or 15% at the other concentrations, for a data point to meet acceptance criteria for use in the linearity curve.

Limit of Detection: The Limit of Detection (LOD) for a metabolite is defined as 1) all replicates for the dilution level and all subsequent levels are observed (i.e., 100% filled) and 2) the average raw ion intensity for the dilution level and all subsequent dilution levels are at least 2× higher than the average intensity of any preceding level. Each of the biochemicals in Tables 1 and 2 were spiked into a surrogate matrix and then extracted. The metabolites were spiked in a serial dilution covering 6 orders of magnitude. The samples were prepared in triplicate on each of the four instrument platforms. Each metabolite (with the exception of caproate and pheynlpropionylglycine—described below) was analyzed in a 6-step serial dilution series with the following concentrations: 0.0404 ng/mL, 0.482 ng/mL, 5.79 ng/mL, 69.4 ng/mL, 833 ng/mL, and 10,000 ng/mL. Caproate was analyzed in a 6-step serial dilution series with the following concentrations: 2.01 ng/mL, 24.1 ng/mL, 289 ng/mL, 3,470 ng/mL, 41,700 ng/mL, 500,000 ng/mL. Phenylpropionylglycine was analyzed in a 6-step serial dilution series with the following concentrations: 2.01 ng/mL, 24.1 ng/mL, 289 ng/mL, 3,470 ng/mL, 41,700 ng/mL, 500,000 ng/mL. The LOD was determined to be the lowest value observed on all four instrument platforms. To meet the acceptance criterion for LOD/LOQ, the measured level of a metabolite must be above the LOD/LOQ.

Matrix Effect/Recovery: To evaluate Matrix Effect/Recovery, each of the biochemicals listed in Table 1 and 2 were spiked into a surrogate matrix and then extracted. The biochemicals were spiked at 1) low and 2) high concentrations into the following solutions: (A) neat solution; (B) post-extraction spiked MTRX QC; (C) pre-extraction spiked MTRX QC; (D) un-spiked MTRX QC. The samples were analyzed on Platform R and the raw ion intensities were used to calculate Matrix Effect (ME), % Recovery (REC) and Overall Process Efficiency (OPE) as follows:

$$\%ME = \frac{(B-D)}{A} \times 100$$

$$\%REC = \frac{C}{B} \times 100$$

Overall Process Efficiency:

$$\%PE = \frac{ME \times RE}{100}$$

The acceptance criteria for matrix effect/recovery was based upon the performance values of % ME, % REC, or % OPE. The acceptance criterion for matrix effect/recovery was as follows: optimal performance is indicated for biochemicals having % ME, % REC and % OPE close to 100% and biochemicals that attain these values meet and surpass the minimum acceptance criteria. To meet acceptance criterion for recovery, the calculated average concentration should be within ±15% of the concentration in QC control. To meet acceptance criterion for matrix effect, the quantitation should not be affected by more than ±15%

Exogenous Interference: Historical data captured using global metabolomics profiling shows that exogenous interferences can be measured independently of other biochemical signatures. That is, data from historical studies reveals that molecules from exogenous interferents such as adhesives and diaper material do not interfere with the chromatographic separation and identification of biochemicals on this platform. In addition, it has been determined that the biochemical identifications made for medications/molecules (e.g. statins, non-steroid anti-inflammatory drugs, pain relievers, antibiotics, antihistamines, and medications for diabetes) do not interfere with the chromatographic separation and biochemical identification of other small molecules on this platform. To meet the acceptance criterion for exogenous interference from exogenous interferents or medications, the % difference between the measured level in the presence of the interferent should be within ±15% of the level measured in the absence of the interferent.

Carryover: Carryover was evaluated on each of the four platforms for each of the biochemicals listed in Table 1 and analyzed as part of the Linearity of Biochemical Standards and Limit of Detection analyses. Specifically, two process blanks were included after the highest standard curve samples in the linearity serial dilution for each analytical run. The first blank acts as an injector carryover sample and the second blank acts as a column carryover blank. Raw ion intensities for the sample with the highest concentration of spiked biochemical (i.e., 10,000 ng/mL) in the LOD/Linearity dilution series, the injector blank, and the carryover blank were determined. The performance value for carryover was calculated using % total carryover. The % total carryover is defined by adding the ion intensities of the two blanks and calculating the percent carryover to the highest concentration in the dilution series. In this example, the following equation was used to calculate % carryover: (Analyte area in process blank)/(Analyte area in Final Replicant Sample in dilution series)×100. If the biochemical is not detected in the carryover sample, it is reported as 0, which indicates there was no carryover.

Because of the dual column configuration of the instrument, the first carryover blank (i.e., INJ_CO) reports the injector carryover and the second carryover blank (i.e., COLUMN_CO) reports the column carryover. The total carryover is the sum of the two.

The calculated performance value obtained for carryover was then compared to an acceptance criterion to determine acceptance of the biochemical for carryover. The acceptance criterion for carryover (described as the compound carryover limit) was as follows: The Compound Carryover Limit (i.e., Cmpd Carryover Limit) was set according to clinically acceptable guidelines that state that an LOD concentration of a compound with a dynamic range of 200 fold cannot be affected by (i.e., have a % total carryover of) >20%. Based on this guidance, and based on the dynamic range of each compound (as determined by multiple patient batch testing), the Cmpd Carryover Limit was established.

Comparison to standard clinical assays (accuracy): When available, measurements for biochemicals were compared to standard CAP/CLIA certified kits used to measure the analyte in clinical/diagnostic laboratories. The standard kits produce quantitative measurements for the analytes. These values were correlated to the semi-quantitative values obtained using global metabolomics profiling. The performance value for comparison to standard clinical assays was calculated using correlation analysis. Correlation analyses were performed between measurements from global metabolomics profiling and standard kit assays. Correlations for each biochemical were calculated and reported. The calculated performance value was then compared to an acceptance criterion to determine acceptance of the biochemical for comparison to standard clinical assays (accuracy). The acceptance criterion for comparison to standard clinical assays (accuracy) was a correlation of 0.8 and higher; biochemicals that meet or exceed this performance value were considered acceptable.

The performance of 276 compounds in plasma and serum samples was assessed and validated according to conventional, currently accepted practices described above. A list of the 276 compounds that were assessed and fully analytically validated in plasma and serum are presented in Table 1. Table 1 also includes the biochemical pathway or sub-family associated with each compound.

TABLE 1

Biochemicals fully analytically validated in plasma and serum and associated biochemical pathways

| Biochemical Name | Biochemical Sub Family |
| --- | --- |
| 1,5-anhydroglucitol (1,5-AG) | Glycolysis, Gluconeogenesis, and Pyruvate Metabolism |
| 12-HETE | Eicosanoid |
| 13-HODE + 9-HODE | Fatty Acid, Monohydroxy |
| 16a-hydroxy DHEA 3-sulfate | Steroid |
| 17alpha-hydroxypregnenolone-3-sulfate | Steroid |
| 1-linoleoyl-GPC (18:2) | Lysolipid |
| 2-aminoadipate | Lysine Metabolism |
| 2-aminoheptanoate | Fatty Acid, Amino |
| 2'-deoxyadenosine | Purine Metabolism, Adenine containing |
| 2'-deoxyguanosine | Purine Metabolism, Guanine containing |
| 2'-deoxyinosine | Purine Metabolism, (Hypo)Xanthine/Inosine containing |
| 2'-deoxyuridine | Pyrimidine Metabolism, Uracil containing |
| 2-hydroxy-3-methylvalerate | Leucine, Isoleucine and Valine Metabolism |
| 2-hydroxybutyrate/2-hydroxyisobutyrate | Glutathione Metabolism |
| 2-hydroxyglutarate | Fatty Acid, Dicarboxylate |
| 2-hydroxyphenylacetate | Phenylalanine and Tyrosine Metabolism |
| 2-methylbutyroylcarnitine (C5) | Leucine, Isoleucine and Valine Metabolism |
| 2-methylcitrate | TCA Cycle |
| 2-methylhippurate | Benzoate Metabolism |
| 2-methylmalonyl carnitine | Fatty Acid Synthesis |
| 2-pyrrolidinone | Chemical |
| 3-(4-hydroxyphenyl)lactate (HPLA) | Phenylalanine and Tyrosine Metabolism |
| 3-(3-hydroxyphenyl)propionate | Benzoate Metabolism |
| 3,4-dihydroxyphenylacetate | Phenylalanine and Tyrosine Metabolism |
| 3-carboxy-4-methyl-5-propyl-2-furanpropanoate (CMPF) | Fatty Acid, Dicarboxylate |
| 3-hydroxy-2-ethylpropionate | Leucine, Isoleucine and Valine Metabolism |
| 3-hydroxy-2-methylbutyrate | Leucine, Isoleucine and Valine Metabolism |
| 3-hydroxybutyrate (BHBA) | Ketone Bodies |
| 3-hydroxyhippurate | Benzoate Metabolism |
| 3-hydroxyisobutyrate | Leucine, Isoleucine and Valine Metabolism |
| 3-hydroxypropanoate | Fatty Acid, Monohydroxy |
| 3-indoxyl-sulfate | Tryptophan Metabolism |
| 3-methyl-2-oxobutyrate | Leucine, Isoleucine and Valine Metabolism |
| 3-methyl-2-oxovalerate | Leucine, Isoleucine and Valine Metabolism |
| 3-methyladipate | Fatty Acid, Dicarboxylate |
| 3-methylcrotonylglycine | Leucine, Isoleucine and Valine Metabolism |
| 3-methylglutaconate | Leucine, Isoleucine and Valine Metabolism |
| 3-methylhistidine | Histidine Metabolism |
| 3-phenylpropionate (hydrocinnamate) | Phenylalanine and Tyrosine Metabolism |
| 3-ureidopropionate | Pyrimidine Metabolism, Uracil containing |
| 4-acetamidobutanoate | Polyamine Metabolism |
| 4-guanidinobutanoate | Guanidino and Acetamido Metabolism |
| 4-hydroxyhippurate | Benzoate Metabolism |
| 4-hydroxyphenylacetate | Phenylalanine and Tyrosine Metabolism |
| 4-hydroxyphenylpyruvate | Phenylalanine and Tyrosine Metabolism |
| 4-methyl-2-oxopentanoate | Leucine, Isoleucine and Valine Metabolism |
| 4-octenedioate | Fatty Acid, Dicarboxylate |
| 4-phenylbutyrate | Drug |
| 4-ureidobutyrate | Pyrimidine Metabolism, Uracil containing |
| 5,6-dihydrouracil | Pyrimidine Metabolism, Uracil containing |
| 5-HETE | Eicosanoid |
| 5-hydroxyhexanoate | Fatty Acid, Monohydroxy |
| 5-methylthioadenosine (MTA) | Polyamine Metabolism |
| 5-oxoproline | Glutathione Metabolism |
| 7-methylguanosine | Purine Metabolism, Guanine containing |
| 9,10-DiHOME | Fatty Acid, Dihydroxy |
| acetylcarnitine (C2) | Fatty Acid Metabolism(Acyl Carnitine) |
| adenine | Purine Metabolism, Adenine containing |
| adenosine | Purine Metabolism, Adenine containing |
| adenosine 5'-monophosphate (AMP) | Purine Metabolism, Adenine containing |
| adenosine-5-diphoshoribose (ADP-ribose) | Purine Metabolism, Adenine containing |

TABLE 1-continued

Biochemicals fully analytically validated in plasma
and serum and associated biochemical pathways

| Biochemical Name | Biochemical Sub Family |
|---|---|
| adipate | Fatty Acid, Dicarboxylate |
| alanine | Alanine and Aspartate Metabolism |
| allantoin | Purine Metabolism, (Hypo)Xanthine/Inosine containing |
| allo-isoleucine | Leucine, Isoleucine and Valine Metabolism |
| alpha-hydroxyisocaproate | Leucine, Isoleucine and Valine Metabolism |
| alpha-hydroxyisovalerate | Leucine, Isoleucine and Valine Metabolism |
| alpha-ketoglutarate | TCA Cycle |
| alpha-tocopherol | Tocopherol Metabolism |
| androsterone sulfate | Steroid |
| anserine | Dipeptide Derivative |
| arabitol/xylitol | Pentose Metabolism |
| arabonate/xylonate | Pentose Metabolism |
| arachidonate (20:4n6) | Polyunsaturated Fatty Acid (n3 and n6) |
| arginine | Urea cycle; Arginine and Proline Metabolism |
| argininosuccinate | Urea cycle; Arginine and Proline Metabolism |
| ascorbate (Vitamin C) | Ascorbate and Aldarate Metabolism |
| asparagine | Alanine and Aspartate Metabolism |
| aspartate | Alanine and Aspartate Metabolism |
| azelate (nonanedioate; C9) | Fatty Acid, Dicarboxylate |
| benzoate | Benzoate Metabolism |
| beta-hydroxyisovalerate | Leucine, Isoleucine and Valine Metabolism |
| beta-hydroxyisovaleroylcarnitine | Leucine, Isoleucine and Valine Metabolism |
| bilirubin | Hemoglobin and Porphyrin Metabolism |
| biliverdin | Hemoglobin and Porphyrin Metabolism |
| biotin | Biotin Metabolism |
| butyrylcarnitine (C4) | Fatty Acid Metabolism (also BCAA Metabolism) |
| caprate (10:0) | Medium Chain Fatty Acid |
| caproate (6:0) | Medium Chain Fatty Acid |
| caprylate (8:0) | Medium Chain Fatty Acid |
| carnitine | Carnitine Metabolism |
| carnosine | Dipeptide Derivative |
| C-glycosyltryptophan | Tryptophan Metabolism |
| chenodeoxycholate | Primary Bile Acid Metabolism |
| cholate | Primary Bile Acid Metabolism |
| cholesterol | Sterol |
| choline | Phospholipid Metabolism |
| cis-4-decenoylcarnitine (C10:1) | Fatty Acid Metabolism(Acyl Carnitine) |
| citrate | TCA Cycle |
| citrulline | Urea cycle; Arginine and Proline Metabolism |
| corticosterone | Steroid |
| cortisol | Steroid |
| cortisone | Steroid |
| creatine | Creatine Metabolism |
| creatinine | Creatine Metabolism |
| cys-gly, oxidized | Glutathione Metabolism |
| cysteine | Methionine, Cysteine, SAM and Taurine Metabolism |
| cysteine-glutathione disulfide | Glutathione Metabolism |
| cysteine-s-sulfate | Methionine, Cysteine, SAM and Taurine Metabolism |
| cystine | Methionine, Cysteine, SAM and Taurine Metabolism |
| cytidine | Pyrimidine Metabolism, Cytidine containing |
| decanoylcarnitine (C10) | Fatty Acid Metabolism(Acyl Carnitine) |
| dehydroisoandrosterone sulfate (DHEA-S) | Steroid |
| deoxycarnitine | Carnitine Metabolism |
| deoxycholate | Secondary Bile Acid Metabolism |
| docosahexaenoate (DHA; 22:6n3) | Polyunsaturated Fatty Acid (n3 and n6) |
| docosapentaenoate (n6 DPA; 22:5n6) | Polyunsaturated Fatty Acid (n3 and n6) |
| dodecanedioate (C12) | Fatty Acid, Dicarboxylate |
| dopamine | Phenylalanine and Tyrosine Metabolism |
| eicosapentaenoate (EPA; 20:5n3) | Polyunsaturated Fatty Acid (n3 and n6) |
| epiandrosterone sulfate | Steroid |
| erythritol | Food Component/Plant |
| ethylmalonate | Leucine, Isoleucine and Valine Metabolism |
| etiocholanolone glucuronide | Steroid |
| fructose | Fructose, Mannose and Galactose Metabolism |
| fumarate | TCA Cycle |
| gamma-aminobutyrate (GABA) | Glutamate Metabolism |
| gamma-glutamylleucine | Gamma-glutamyl Amino Acid |
| gamma-glutamylmethionine | Gamma-glutamyl Amino Acid |

TABLE 1-continued

Biochemicals fully analytically validated in plasma
and serum and associated biochemical pathways

| Biochemical Name | Biochemical Sub Family |
| --- | --- |
| gamma-glutamylphenylalanine | Gamma-glutamyl Amino Acid |
| gamma-glutamylvaline | Gamma-glutamyl Amino Acid |
| glucose | Glycolysis, Gluconeogenesis, and Pyruvate Metabolism |
| glutamate | Glutamate Metabolism |
| glutamine | Glutamate Metabolism |
| glutarate (pentanedioate) | Lysine Metabolism |
| glutaroylcarnitine (C5) | Lysine Metabolism |
| glycerate | Glycolysis, Gluconeogenesis, and Pyruvate Metabolism |
| glycerol | Glycerolipid Metabolism |
| glycerophosphorylcholine (GPC) | Phospholipid Metabolism |
| glycine | Glycine, Serine and Threonine Metabolism |
| glycochenodeoxycholate | Primary Bile Acid Metabolism |
| glycocholate | Primary Bile Acid Metabolism |
| glycodeoxycholate | Secondary Bile Acid Metabolism |
| glycohyocholate | Secondary Bile Acid Metabolism |
| glycolithocholate | Secondary Bile Acid Metabolism |
| glycoursodeoxycholate | Secondary Bile Acid Metabolism |
| guanidinoacetate | Creatine Metabolism |
| guanidinosuccinate | Guanidino and Acetamido Metabolism |
| guanosine | Purine Metabolism, Guanine containing |
| heme | Hemoglobin and Porphyrin Metabolism |
| heptanoate (7:0) | Medium Chain Fatty Acid |
| heptanoyl glycine | Fatty Acid Metabolism(Acyl Glycine) |
| hexadecanedioate (C16) | Fatty Acid, Dicarboxylate |
| hexanoylcarnitine (C6) | Fatty Acid Metabolism(Acyl Carnitine) |
| hexanoylglycine (C6) | Fatty Acid Metabolism(Acyl Glycine) |
| hippurate | Benzoate Metabolism |
| histidine | Histidine Metabolism |
| homoarginine | Urea cycle; Arginine and Proline Metabolism |
| homocitrulline | Urea cycle; Arginine and Proline Metabolism |
| hypoxanthine | Purine Metabolism, (Hypo)Xanthine/Inosine containing |
| indoleacetate | Tryptophan Metabolism |
| indoleacetylglutamine | Tryptophan Metabolism |
| indolelactate | Tryptophan Metabolism |
| indolepropionate | Tryptophan Metabolism |
| inosine | Purine Metabolism, (Hypo)Xanthine/Inosine containing |
| isobutyrylcarnitine (C4) | Leucine, Isoleucine and Valine Metabolism |
| isobutyrylglycine (C4) | Leucine, Isoleucine and Valine Metabolism |
| isoleucine | Leucine, Isoleucine and Valine Metabolism |
| isovalerate (C5) | Leucine, Isoleucine and Valine Metabolism |
| isovalerylcarnitine (C5) | Leucine, Isoleucine and Valine Metabolism |
| isovalerylglycine | Leucine, Isoleucine and Valine Metabolism |
| kynurenate | Tryptophan Metabolism |
| kynurenine | Tryptophan Metabolism |
| lactate | Glycolysis, Gluconeogenesis, and Pyruvate Metabolism |
| laurylcarnitine (C12) | Fatty Acid Metabolism(Acyl Carnitine) |
| leucine | Leucine, Isoleucine and Valine Metabolism |
| linoleate (18:2n6) | Polyunsaturated Fatty Acid (n3 and n6) |
| linolenate (18:3n3 or 3n6) | Polyunsaturated Fatty Acid (n3 and n6) |
| lysine | Lysine Metabolism |
| malate | TCA Cycle |
| mannose | Fructose, Mannose and Galactose Metabolism |
| methionine | Methionine, Cysteine, SAM and Taurine Metabolism |
| methionine sulfone | Methionine, Cysteine, SAM and Taurine Metabolism |
| methionine sulfoxide | Methionine, Cysteine, SAM and Taurine Metabolism |
| methyl-4-hydroxybenzoate | Benzoate Metabolism |
| methylmalonate (MMA) | Fatty Acid Metabolism (also BCAA Metabolism) |
| methylsuccinate | Leucine, Isoleucine and Valine Metabolism |
| myo-inositol | Inositol Metabolism |
| myristoleate (14:1n5) | Long Chain Fatty Acid |
| myristoylcarnitine (C14) | Fatty Acid Metabolism(Acyl Carnitine) |
| N1-methyladenosine | Purine Metabolism, Adenine containing |
| N2,N2-dimethylguanosine | Purine Metabolism, Guanine containing |
| N2-acetyllysine | Lysine Metabolism |
| N2-methylguanosine | Purine Metabolism, Guanine containing |
| N6-acetyllysine | Lysine Metabolism |
| N6,N6,N6-trimethyllysine | Lysine Metabolism |

TABLE 1-continued

Biochemicals fully analytically validated in plasma and serum and associated biochemical pathways

| Biochemical Name | Biochemical Sub Family |
|---|---|
| N6-succinyladenosine | Purine Metabolism, Adenine containing |
| N-acetylalanine | Alanine and Aspartate Metabolism |
| N-acetylarginine | Urea cycle; Arginine and Proline Metabolism |
| N-acetylglycine | Glycine, Serine and Threonine Metabolism |
| N-acetylleucine | Leucine, Isoleucine and Valine Metabolism |
| N-acetylneuraminate | Aminosugar Metabolism |
| N-acetylphenylalanine | Phenylalanine and Tyrosine Metabolism |
| N-acetylserine | Glycine, Serine and Threonine Metabolism |
| N-acetylthreonine | Glycine, Serine and Threonine Metabolism |
| N-acetyltyrosine | Phenylalanine and Tyrosine Metabolism |
| N-carbamoylaspartate | Pyrimidine Metabolism, Orotate containing |
| N-formylmethionine | Methionine, Cysteine, SAM and Taurine Metabolism |
| nicotinamide | Nicotinate and Nicotinamide Metabolism |
| N-octanoylglycine | Fatty Acid Metabolism(Acyl Glycine) |
| octadecanedioate (C18) | Fatty Acid, Dicarboxylate |
| octanoylcarnitine (C8) | Fatty Acid Metabolism(Acyl Carnitine) |
| oleate/vaccenate (18:1) | Long Chain Fatty Acid |
| oleoylcarnitine (18:1) | Fatty Acid Metabolism(Acyl Carnitine) |
| ornithine | Urea cycle; Arginine and Proline Metabolism |
| orotate | Pyrimidine Metabolism, Orotate containing |
| palmitoleate (16:1n7) | Long Chain Fatty Acid |
| palmitoylcarnitine | Fatty Acid Metabolism(Acyl Carnitine) |
| palmitoyl sphingomyelin (d18:1/16:0) | Sphingolipid Metabolism |
| pelargonate (9:0) | Medium Chain Fatty Acid |
| phenylacetate | Phenylalanine and Tyrosine Metabolism |
| phenylacetylglutamine | Phenylalanine and Tyrosine Metabolism |
| phenylacetylglycine | Phenylalanine and Tyrosine Metabolism |
| phenylalanine | Phenylalanine and Tyrosine Metabolism |
| phenylalanylphenylalanine | Dipeptide |
| phenyllactate (PLA) | Phenylalanine and Tyrosine Metabolism |
| phenylpropionylglycine | Phenylalanine and Tyrosine Metabolism |
| phenylpyruvate | Phenylalanine and Tyrosine Metabolism |
| pregnanediol-3-glucuronide | Steroid |
| pregnenolone sulfate | Steroid |
| pro-hydroxy-pro | Urea cycle; Arginine and Proline Metabolism |
| proline | Urea cycle; Arginine and Proline Metabolism |
| propionylcarnitine (C3) | Fatty Acid Metabolism (also BCAA Metabolism) |
| propionylglycine (C3) | Fatty Acid Metabolism (also BCAA Metabolism) |
| pseudouridine | Pyrimidine Metabolism, Uracil containing |
| pyridoxate | Vitamin B6 Metabolism |
| quinolinate | Nicotinate and Nicotinamide Metabolism |
| retinol (Vitamin A) | Vitamin A Metabolism |
| ribose | Pentose Metabolism |
| S-adenosylhomocysteine (SAH) | Methionine, Cysteine, SAM and Taurine Metabolism |
| sebacate (decanedioate) | Fatty Acid, Dicarboxylate |
| serine | Glycine, Serine and Threonine Metabolism |
| serotonin | Tryptophan Metabolism |
| stearoylcarnitine (C18) | Fatty Acid Metabolism(Acyl Carnitine) |
| suberate (octanedioate) | Fatty Acid, Dicarboxylate |
| succinate | TCA Cycle |
| succinimide | Chemical |
| succinylcarnitine (C4) | TCA Cycle |
| taurine | Methionine, Cysteine, SAM and Taurine Metabolism |
| taurochenodeoxycholate | Primary Bile Acid Metabolism |
| taurocholate | Primary Bile Acid Metabolism |
| taurodeoxycholate | Secondary Bile Acid Metabolism |
| taurolithocholate 3-sulfate | Secondary Bile Acid Metabolism |
| tetradecanedioate (C14) | Fatty Acid, Dicarboxylate |
| threonate | Ascorbate and Aldarate Metabolism |
| threonine | Glycine, Serine and Threonine Metabolism |
| thymidine | Pyrimidine Metabolism, Thymine containing |
| thymine | Pyrimidine Metabolism, Thymine containing |
| thyroxine | Phenylalanine and Tyrosine Metabolism |
| tigloylglycine | Leucine, Isoleucine and Valine Metabolism |
| tiglyl carnitine (C5) | Leucine, Isoleucine and Valine Metabolism |
| trans-4-hydroxyproline | Urea cycle; Arginine and Proline Metabolism |
| trans-urocanate | Histidine Metabolism |
| trimethylamine N-oxide | Phospholipid Metabolism |
| tryptophan | Tryptophan Metabolism |
| tyramine | Phenylalanine and Tyrosine Metabolism |
| tyrosine | Phenylalanine and Tyrosine Metabolism |
| uracil | Pyrimidine Metabolism, Uracil containing |

TABLE 1-continued

Biochemicals fully analytically validated in plasma and serum and associated biochemical pathways

| Biochemical Name | Biochemical Sub Family |
|---|---|
| urate | Purine Metabolism, (Hypo)Xanthine/Inosine containing |
| urea | Urea cycle; Arginine and Proline Metabolism |
| uridine | Pyrimidine Metabolism, Uracil containing |
| ursodeoxycholate | Secondary Bile Acid Metabolism |
| valerylphenylalanine | Dipeptide |
| valine | Leucine, Isoleucine and Valine Metabolism |
| xanthine | Purine Metabolism, (Hypo)Xanthine/Inosine containing |
| xanthosine | Purine Metabolism, (Hypo)Xanthine/Inosine containing |

Multiple studies were carried out to assess the performance of a total of 176 compounds in urine and CSF samples. In these studies the analytical performance for the analytes was assessed and validated according to conventional, currently accepted practices described above. A representative list of 132 compounds that were assessed and fully analytically validated in a first analysis in CSF and urine are presented in Table 2. Table 2 also includes the biochemical pathway associated with each compound.

TABLE 2

Biochemicals fully analytically validated and associated biochemical pathways (urine and CSF)

| Biology Family | Biochemical |
|---|---|
| Carbohydrate, Glycosis | 1,5-anhydroglucitol (1,5-AG) |
| Nucleotide | 2'-deoxyadenosine |
| Nucleotide, Purine Metabolism | 2'-deoxyinosine |
| Nucleotide | 2'-deoxyguanosine |
| Amino Acid, Lysine Metabolism | 2-aminoadipate |
| Lipid, fatty acid | 2-aminoheptanoate |
| Amino Acid, BCAA Metabolism | 2-hydroxy-3-methylvalerate |
| Lipid, Fatty acid dicarboxylate | 2-hydroxyglutarate |
| Amino Acid, Aromatic Amino Acid Metabolism | 2-hydroxyphenylacetate |
| Amino Acid, BCAA Metabolism | 2-methylbutyrylcarnitine (C5) |
| Energy TCA Cycle | 2-methylcitrate |
| Xenobiotic, Benzoate Metabolism | 2-methylhippurate |
| Lipid, Fatty Acid Synthesis | 2-methylmalonyl carnitine |
| Amino Acid, Aromatic Amino Acid Metabolism | 2-pentamido-3-phenylpropanoic acid |
| Amino Acid, Aromatic Amino Acid Metabolism | 3-(3-hydroxyphenyl)propionate |
| Amino Acid, Aromatic Amino Acid Metabolism | 3-(4-hydroxyphenyl)lactate |
| Amino Acid, Aromatic Amino Acid Metabolism | 3,4-dihydroxyphenylacetate |
| Amino Acid, BCAA Metabolism | 3-hydroxy-2-methylbutyrate |
| Amino Acid, BCAA Metabolism | 3-hydroxy-2-methylpropionate |
| Lipid, Ketone Body | 3-hydroxybutyrate |
| Amino Acid, BCAA Metabolism | 3-hydroxyisobutyrate |
| Lipid, Monohydroxy fatty acid | 3-hydroxypropanoate |
| Amino Acid, BCAA Metabolism | 3-methyl-2-oxobutyrate |
| Amino Acid, BCAA Metabolism | 3-methyl-2-oxovalerate |
| Lipid, Dicarboxylic acid | 3-methyladipate |
| Amino Acid, BCAA Metabolism | 3-methylcrotonylglycine |
| Nucleotide, Pyrimidine Metabolism | 3-ureidopropionate |
| Urea Cycle, Energy Metabolism | 3-guanidinobutanoate |
| Amino Acid, Aromatic Amino Acid Metabolism | 4-hydroxyphenylacetate |
| Amino Acid, Aromatic Amino Acid Metabolism | 4-hydroxyphenylpyruvate |
| Amino Acid, BCAA Metabolism | 4-methyl-2-oxopentanoate |
| Lipid, Dicarboxylic acid | 4-octenedioate |
| Xenobiotic, Benzoate Metabolism | 4-phenylbutyrate |
| Nucleotide, Pyrimidine Metabolism | 4-ureidobutyrate |
| Nucleotide, Pyrimidine Metabolism | 5,6-dihydrouracil |
| Lipid, Monohydroxy fatty acid | 5-hydroxyhexanoate |
| Amino Acid, Polyamine Metabolism | 5-methylthioadenosine (MTA) |
| Nucleotide, Purine Metabolism | 7-methylguanosine |
| Lipid, Acylcarnitine | acetylcarnitine |
| Nucleotide, Purine Metabolism | adenine |
| Nucleotide, Purine Metabolism | Adenosine |
| Lipid, Dicarboxylic acid | Adipate |
| Nucleotide, Purine Metabolism | Allantoin |
| Amino Acid, BCAA Metabolism | allo-isoleucine |
| Amino Acid, BCAA Metabolism | alpha-hydroxyisocaproate |
| Amino Acid, BCAA Metabolism | alpha-hydroxyisovalerate |
| Lipid, Polyunsatured Fatty Acid | arachidonate (20:4n6) |

TABLE 2-continued

Biochemicals fully analytically validated and
associated biochemical pathways (urine and CSF)

| Biology Family | Biochemical |
| --- | --- |
| Amino Acid, Urea Cycle | Arginine |
| Amino Acid, Urea Cycle | argininosuccinate |
| Amino Acid, Alanine & Aspartate Metabolism | Asparagine |
| Amino Acid, Alanine & Aspartate Metabolism | Aspartate |
| Xenobiotic, Drug | Benzoate |
| Amino Acid, BCAA Metabolism | beta-hydroxyisovalerate |
| Vitamin and Cofactor | Biotin |
| Lipid, Carnitine | Carnitine |
| Amino Acid, Urea Cycle | citrulline |
| Urea Cycle, Energy Metabolism | creatine |
| Urea Cycle, Energy Metabolism | creatinine |
| Glutathione Metabolism | cysteine-S-sulfate |
| Nucleotide, Pyrimidine Metabolism | cytidine |
| Lipid, Acylcarnitine | decanoylcarnitine (C10) |
| Lipid, Carnitine metabolism | deoxycarnitine |
| Amino Acid, BCAA Metabolism | ethylmalonate |
| Petptide, gamm-glutamyl amino acid | gamma-glutamylphenylalanine |
| Amino Acid, Glutamate & Glutamine Metabolism | glutamine |
| Amino Acid, Lysine Metabolism | glutarate (pentanedioate) |
| Amino Acid, Lysine Metabolism | glutarylcarnitine (C5) |
| Amino Acid, Urea Cycle | Guanidinoacetate |
| Amino Acid, Guanidino Metabolism | guanidinosuccinate |
| Nucleotide, Purine Metabolism | guanosine |
| Lipid, Acyl glycine | heptanoylglycine |
| Benzoate Metabolism | hippurate |
| Urea Cycle | homocitruline |
| Nucleotide, Purine Metabolism | Hypoxanthine |
| Nucleotide, Purine Metabolism | inosine |
| Amino Acid, BCAA Metabolism | isobutyrylcarnitine |
| Amino Acid, BCAA Metabolism | isoleucine |
| Amino Acid, BCAA Metabolism | isovalerate |
| Amino Acid, BCAA Metabolism | isovalerylcarnitine |
| Amino Acid, BCAA Metabolism | isovalerylglycine |
| Carbohydrate, Glycolysis | lactate |
| Lipid, Acylcarnitine Metabolism | laurylcarnitine |
| Amino Acid, BCAA Metabolism | leucine |
| Amino Acid, Lysine Metabolism | lysine |
| Amino Acid, Sulfur Metabolism | methionine |
| Xenobiotic, Benzoate Metabolism | Methyl-4-hydroxybenzoate |
| Lipid, Acylcarnitine Metabolism | methylmalonate |
| Amino Acid, BCAA Metabolism | methylsuccinate |
| Lipid, Acylcarnitine | myristoylcarnitine |
| Nucleotide | N1-methyladenosine |
| Nucleotide, Purine Metabolism | N2,N2-dimethylguanosine |
| Amino Acid, Lysine Metabolism | N2-acetyllsine |
| Nucleotide, Purine Metabolism | N2-methylguanosine |
| Amino Acid, Lysine Metabolism | N6-acetyllysine |
| Nucleotide, Purine Metabolism | N6-succinyladenosine |
| Amino Acid, Lysine Metabolism | N6-trimethyllysine |
| Amino Acid, Urea Cycle | N-acetylarginine |
| Amino Acid, BCAA Metabolism | N-acetylleucine |
| Amino Acid, Aromatic Amino Acid Metabolism | N-acetylphenylalanine |
| Nucleotide, Pyrimidine Metabolism | N-carbamoylaspartate |
| Lipid, Acylcarnitine | N-octanoylglycine (C8 ester) |
| Lipid, Acylcarnitine Metabolism | octanoylcarnitine (C8) |
| Amino Acid, Urea Cycle | ornithine |
| Nucleotide, Pyrimidine Metabolism | orotate |
| Lipid, Acylcarnitine | palmitoylcarnitine |
| Amino Acid, Aromatic Amino Acid Metabolism | phenylacetylglutamine |
| Amino Acid, Aromatic Amino Acid Metabolism | phenylacetyglycine |
| Amino Acid, Aromatic Amino Acid Metabolism | phenylalanine |
| Amino Acid, Aromatic Amino Acid Metabolism | phenyllactate (PLA) |
| Amino Acid, Aromatic Amino Acid Metabolism | phenylpropionylglycine |
| Dipeptide | pro-hydroxy-pro |
| Amino Acid, BCAA Metabolism | propioniylglycine |
| Amino Acid, BCAA Metabolism | propionylcarnitine |
| Amino Acid, Sulfur Metabolism | S-adenosylhomocysteine (SAH) |
| Lipid, Dicarboxylic Acid | sebacate (C8) |
| Lipid, Dicarboxylic Acid | suberate (octanedioate) |
| Energy, TCA cycle | succinate |
| Xenobiotic, Chemical | Succinimde |
| Energy, TCA Cycle | succinylcarnitine |
| Nucleotide, Pyrimidine | thymine |
| Amino Acid, BCAA Metabolism | tigloylglycine |
| Amino Acid, BCAA Metabolism | tiglyl carnitine |

TABLE 2-continued

Biochemicals fully analytically validated and
associated biochemical pathways (urine and CSF)

| Biology Family | Biochemical |
|---|---|
| Amino Acid, Proline | trans-4-hydroxyproline |
| Choline Metabolism | Trimethylamine N-oxide |
| Amino Acid, Aromatic Amino Acid Metabolism | tyrosine |
| Nucleotide, Pyrimidine | uracil |
| Nucleotide, Purine Metabolism | urate |
| Amino Acid, Urea Cycle | urea |
| Nucleotide, Pyrimidine Metabolism | uridine |
| Amino Acid, BCAA Metabolism | valine |
| Nucleotide, Purine Metabolism | Xanthine |
| Nucleotide, Purine Metabolism | xanthosine |

In addition, the full validation analysis was performed on multiple platforms to determine inter-platform precision and to assess the reproducibility of the validation across multiple instrument systems. The acceptance criterion for inter-platform precision was based on the calculated % CV. The inter-platform precision (% CV) varied by metabolite and ranged from a low of 2.7% to a high of 297%. However, the inter-platform precision for the vast majority of the metabolites was less than 40%, (242 of 276) with most less than 20% (234 of 276).

Summarized in Table 3 are exemplary analytical validation conditions, the analysis performed for each condition, acceptance criteria and result (pass/fail) obtained for the analytes listed in Table 1 and Table 2. The analytical validation analysis was performed on blood (plasma, serum), urine and CSF samples to determine matrix effects.

TABLE 3

Analytical Validation Conditions, Analysis Performed, Acceptance Criteria and Results

| Analytical Validation Condition | Analysis Performed | Acceptance Criteria | Result |
|---|---|---|---|
| Precision (Intra-day) | Determine % Coefficient of Variation (CV) for each sample | All % CVs ≤ 25% | Pass |
| Precision (Inter-day) | Determine % CV for each sample across all days and for each day | All % CVs ≤ 25% | Pass |
| Linearity of Calibration Standards | 1. Plot the actual concentrations against the expected concentrations to see if the results are linear; determine the $R^2$ value<br>2. Calculate the % Systematic Error (SE): [(Actual − Theoretical)/Theoretical] × 100] | 1. $R^2 \leq 0.8$<br>2. % SE should be within ±20% at the lowest concentration point and ±15% at the other concentrations | 1. Pass<br>2. Pass |
| Linearity of Patient Specimens | 1. Plot the actual concentrations against the expected concentrations to see if the results are linear; determine the $R^2$ value<br>2. Calculate the % SE | 1. $R^2 \geq 0.8$<br>2. % SE should be within ±20% at concentrations between the low and high QC levels | 1. Pass<br>2. Pass |
| Limit of Detection/Quantitation | 1. The % CV will be determined for each sample, for both intra-day and inter-day.<br>2. Determine the signal-to-noise ratio for each result. | 1. The % CV of each sample at the LLOQ must not exceed 25%<br>2. The signal-to-noise ratio must be at least 3:1 | 1. Pass<br>2. Pass |
| Recovery | Back calculate the original analyte concentration in the overspiked QC sample & determine the % bias: [(Level X − Control)/Control] × 100 | Calculated average concentration should be within ±15% of the concentration in QC control | Pass |

TABLE 3-continued

Analytical Validation Conditions, Analysis Performed, Acceptance Criteria and Results

| Analytical Validation Condition | Analysis Performed | Acceptance Criteria | Result |
|---|---|---|---|
| Interference Studies | 1. Calculate % bias for each level<br>2. Spike therapeutic levels of pharmaceuticals into low and high QC and evaluate % bias against control low and high QC<br>3. Compare each matrix tube type and calculate the % difference: [(Type 1 − Type 2)/Average] × 100<br>4. Check for the presence of a peak at the retention times of the analytes by extracting water & low and high QC samples that have been stored in the varying tube types<br>5. Spike blank sample with the isomers and check for interference at the retention time of the analytes. If an interference exists at a similar retention time to the analytes, spike low and high QC samples with the approximate biological level of the isomer and verify that quantitation of the QC is not affected. | 1. % Bias should not exceed ±15%<br>2. % Bias should not exceed ±15%<br>3. % Difference should not exceed ±15%<br>4. Absence of MS peak where analyte peaks elute when extracting water. For matrix, quantitation should not be affected by more than ±15%.<br>5. Absence of MS peak where analyte peaks elute. If QC spiking is necessary, then accuracy of the analyte quantitation in the QC should not be affected by more than ±15%. | 1. Hemolysis - all analytes pass Lipemia - pass<br>2. Pass<br>3. All analytes pass<br>4. No peaks greater than the LLOQ were detected near the retention times of the analytes or internal standards. % Bias was acceptable for all analytes in matrix.<br>5. No interference exists with any of the isomers. QC spiking was not necessary. |
| Sample Stability Testing | Freeze-thaw stability: Freeze-thaw stability was tested in previous validations, and the impact of multiple freeze-thaws found to be significant for the subset of analytes tested in those validations. Freeze-thaw is not recommended for these samples. Because of that, freeze-thaw was not tested in this validation.<br>4° C./Ice bath stability: Triplicate samples of two plasma QC samples stored at 4° C. for 1, 2, 4, and 24 hours were analyzed. | Calculated % difference for each sample stability testing protocol: [(Time point X − Time Point 0)/ (Time point 0)] × 100 = % Difference | Pass<br>Pass |
| Carryover | Carryover was evaluated on each of the four platforms for each of the biochemicals listed in Table 1 and analyzed as part of the the Linearity of Biochemical Standards and Limit of Detection sections (see above). Specifically, two process blanks were included after the highest standard | Raw ion intensities for the sample with the highest concentration of spiked compound (i.e., 10,000 ng/mL) in the LOD/Linearity dilution series, the injector blank, and the carryover blank were determined. % total carryover is defined by adding the ion intensities of the two blanks and calculating the | Pass |

TABLE 3-continued

Analytical Validation Conditions, Analysis Performed, Acceptance Criteria and Results

| Analytical Validation Condition | Analysis Performed | Acceptance Criteria | Result |
|---|---|---|---|
| | curve samples in the linearity serial dilution for each run. The first blank acts as an injector carryover samples and the second blank acts as a column carryover blank. | percent carryover to the high concentration in the dilution series. Analyte area in process blank)/(Analyte area in Final Rep in dilution series) × 100. | |

Example 2

Streamlined Assessment of Biochemical Performance

Following full analytical validation described in Example 1, a streamlined analytical validation analysis was performed to assess inter-day precision and intra-day precision. The performance of the fully analytically-validated compounds (Table 1 and Table 2) was used to assess the performance of about 4,000 biochemicals. Performance of the approximately 4000 biochemicals was assessed using two analytical validation conditions: intra-day precision and inter-day precision. Performance values for intra-day and inter-day precision were calculated based on the percent fill (% fill) and CV for each of the biochemicals. Acceptance criteria for intra-day precision for % fill was based on detection of the biochemical in all or most (e.g. 70% or more, preferably 80% or more) of the technical replicate samples run in a single day (referred to herein as a run-day). Acceptance criteria for intra-day precision for CV was less than or equal to 30% CV. Acceptance criteria for inter-day precision for % fill was based on detection of the biochemical in all or most of the replicate samples run over multiple days (e.g. 70% or more, preferably 80% or more). Acceptance criteria for inter-day precision for CV were determined to be equal to or less than 25% CV.

Intra-day Precision Analysis. For the intra-day precision analysis, 4 technical replicates of a pooled reference sample were used for each of plasma, urine, and CSF in ten separate run-days.

Acceptance criteria for intra-day precision analysis of a biochemical was based on detection of the biochemical in technical replicate samples run in a single day. Biochemicals detected in all 4 (100% fill) of the technical replicate samples run in a single day were determined to meet the % fill acceptance criterion for intra-day precision. The % CV was also used to assess performance. Biochemicals determined to have a CV of 30% or less were determined to meet the % CV acceptance criterion and have acceptable performance for intra-day precision.

Intra-day precision was assessed for biochemicals in plasma samples (N=40) analyzed by LC-MS as described in the General Methods section. 670 unique biochemicals were detected in 100% of technical replicate samples (i.e., 100% fill) on a single day and were determined to meet the % fill acceptance criterion and have acceptable performance for intra-day precision. The mean % CV for these 670 biochemicals was 10.1%, and the median was 7.2%.

Using a subset of the samples, performance of the biochemicals for intra-day precision was assessed based on % CV and % fill acceptance criteria. In this subset of samples, 580 biochemicals were detected in 100% of technical replicate samples on a single day. Of these 580 analytes, 166 were previously analytically validated (Table 1) while 414 were not previously validated. Of the 414 not previously analytically validated, 387 had % CV of <30%. These 387 biochemicals were determined to meet the acceptance criteria and have acceptable performance for intra-day precision (100% fill, % CV<30), indicating that the described streamlined performance assessment using intra-day precision can expand the number of analytically validated molecules in serum and plasma in a streamlined, efficient manner.

For example, isovalerate was not fully analytically validated in the initial full assessment. In the streamlined assessment, the % fill was 100% and the % CV of isovalerate ranged from 0.9% to 15% in plasma samples, with a mean of 5.1% and a median of 3.1%. Using these performance measures, isovalerate was determined to be acceptable for analytical validation using the streamlined assessment. In the same samples, isovalerylcarnitine, a molecule biochemically related to isovalerate and previously fully analytically validated using the full set of conditions, the % fill was 100% and the CV ranged from 3% to 14.4%, a mean of 7.5% and a median of 7.1%.

Additional exemplary biochemicals detected in all or most of the samples (% fill) that were assessed include: 1) Pipecolate had a % CV range of 0.9% to 11.7%, a mean of 6%, and a median of 5.9%, 2) 4 molecules related to tyrosine metabolism were fully analytically validated, and 10 related analytes assessed in the streamlined analysis were detected in the intra-day precision analysis and all 10 showed low CV; 3) related to the Urea cycle; Arginine and Proline Metabolism—8 molecules were assessed and validated in the full analysis, and 4 other molecules were detected in the streamlined analysis and all four showed low CV; 4) related to Carbohydrate metabolism—9 molecules across 4 subfamilies were validated using full assessment; 10 additional molecules were validated using the streamlined analysis.

The intra-day precision was determined for biochemicals in urine samples (N=40) analyzed by LC-MS as described in the General Methods section above. 568 unique biochemicals that were detected in 100% of technical replicate samples (i.e., 100% fill) on a single day were determined to have acceptable performance for intra-day precision. The mean % CV for these 568 biochemicals was 8.1%, and the median was 5.9%.

Using a subset of the samples, performance of the biochemicals for intra-day precision was assessed based on % CV and % fill. In this sample subset, 442 biochemicals were detected in 100% of technical replicate samples on a single day. Of these 442 analytes, 138 were validated using the full analysis described in Example 1, while 304 biochemicals had not been previously validated. Of the 304 not previously validated, 296 had % CV of <30%. These 296 biochemicals were determined to meet acceptance criteria for % fill and % CV and have acceptable performance for intra-day precision, indicating that the described streamlined performance assessment using intra-day precision can be used to expand the number of analytically validated molecules in urine in a streamlined, efficient manner.

For example, dihydrobiopterin was not assessed in previous full analytical validation studies. It was detected in all of the samples (100% fill) and the % CV of dihydrobiopterin ranged from 2.2% to 20.8% in urine samples with a mean of 7.9% and a median of 7.1%. Using these performance measures, dihydrobiopterin was determined to meet acceptance criteria and was acceptable for analytical validation using the streamlined analysis. In the same samples, glucose, a molecule biochemically related to dihydrobiopterin and previously validated using the full set of conditions, had a CV ranging from 2.2% to 14.7%, a mean of 6.3% and a median of 4.7%.

Additional examples include: 1) Glutamate metabolism subfamily: Glutamine and 2-pyrrolidinone were validated using the full assessment. Biochemically-related molecules N-acetylglutamine, pyroglutamine, glutamate, gamma-carboxyglutamate, N-acetyl-aspartyl-glutamate (NAAG), carboxyethyl-GABA, N-acetylglutamate, N-methyl-GABA, and 4-hydroxyglutamate were also measured in the samples, and all had <30% CV when assessed using the streamlined method; 2) Another superfamily with expanded biochemical coverage was the lipid superfamily that includes several subfamilies such as primary and secondary bile acids, dicarboxylic acids and the nucleotide superfamily.

Intra-day precision was determined for biochemicals in CSF samples (N=40) analyzed by LC-MS as described in the General Methods section above. A total of 346 unique biochemicals that were detected in 100% of technical replicate samples on a single day were determined to meet acceptance criteria and have acceptable performance for intra-day precision. The mean % CV for these 346 biochemicals was 11.8%, and the median was 8.6%.

Using a subset of the samples, performance of the biochemicals for intra-day precision was assessed. In this subset of samples, 286 biochemicals were detected in 100% of technical replicate samples on a single day. Of these 286 analytes, 94 were fully analytically validated while 192 were not validated in the full assessment. Of the 192 not fully validated, 182 had % CV of <30%. These 182 biochemicals were determined to meet % fill and % CV acceptance criteria and have acceptable performance for intra-day precision, indicating that the described streamlined performance assessment using intra-day precision can be used to expand the number of analytically validated molecules in CSF in a streamlined, efficient manner.

For example, acetylcarnitine was not assessed in full analytical validation studies. It was detected in all of the samples and the % CV of acetylcarnitine ranged from 2.1% to 25.8% in CSF samples with a mean of 13% and a median of 10.5%. Using these performance measures, acetylcarnitine was determined to meet acceptance criteria and be acceptable for analytical validation using the streamlined analysis. In the same samples, glutamine, a molecule biochemically related to acetylcarnitine and previously validated using the full set of conditions, had a CV ranging from 2% to 7.8%, a mean of 5.3% and a median of 5.5%.

Additional examples of metabolites that were assessed and analytically validated using the streamlined validation include: 1) Biochemicals in the glycine, serine and threonine metabolism subfamily: betaine, dimethylglycine, glycine, N-acetylglycine, N-acetylserine, N-acetylthreonine, serine, and threonine; 2) Biochemicals in the tyrosine metabolism subfamily: 3-(4-hydroxyphenyl)lactate, 3-methoxytyramine sulfate, 3-methoxytyrosine, dopamine 3-O-sulfate, homovanillate (HVA), phenol sulfate, and tyrosine. Tyrosine and 3-(4-hydroxyphenyl) lactate were evaluated in the full analyses and passed the full analytical validation studies as well.

Inter-day precision analysis. For the inter-day precision analysis, 30 plasma samples, 44 urine samples, and 32 CSF samples were analyzed in two independent analyses.

Acceptance criteria for inter-day precision analysis of a biochemical was based on detection of the biochemical in technical replicate samples across fifteen sample run-days. Biochemicals detected in at least 80% of the technical replicate samples across all fifteen sample run-days (i.e., 80% fill) were determined to meet the % fill acceptance criterion and have acceptable performance for inter-day precision. An alternative acceptance criterion based on % CV was also used. Biochemicals determined to have a CV of less than 25% were determined to meet the % CV acceptance criterion and have acceptable performance for inter-day precision.

Inter-day precision was assessed for biochemicals in plasma samples analyzed by LC-MS as described in the General Methods section above. In one example, using 30 plasma samples, 523 biochemicals met the % fill acceptance criterion of being detected in at least 80% of the samples analyzed over multiple days. Performance of all of these biochemicals for inter-day precision was further assessed using CV. In this example, 443 of the 523 biochemicals also had a CV of less than 25% and were determined to meet the % CV acceptance criterion and have acceptable performance for inter-day precision; 163 of the 443 represented molecules that were fully analytically validated (Table 1). There were 280 biochemicals not fully validated that were determined to meet acceptance criteria and have acceptable performance for inter-day precision using the described methods for streamlined performance assessment.

In another example, using an independent set of 30 plasma samples, 507 biochemicals met the % fill criterion of being detected in at least 80% of the samples analyzed over multiple days. Performance of all of these biochemicals for inter-day precision was further assessed using CV. In this example, 410 of the 507 biochemicals also had a CV of less than 25% and were determined to meet acceptance criterion for % CV and have acceptable performance for inter-day precision; 148 of the 410 represent molecules that were fully analytically validated (Table 1). There were 262 biochemicals not fully validated that were determined to meet acceptance criteria and have acceptable performance for inter-day precision using the described methods for streamlined performance assessment.

Inter-day precision was assessed for biochemicals in urine samples analyzed by LC-MS as described in the General Methods section above. In one example, using 44 urine samples, 457 biochemicals met the % fill acceptance criterion of being detected in at least 80% the samples analyzed over multiple days. Performance of all of these biochemicals for inter-day precision was further assessed using CV. In this example, 408 of the 457 biochemicals also had a CV of less than 25% and were determined to meet the acceptance criterion and have acceptable performance for inter-day precision; 162 of the 408 represent molecules that were fully analytically validated. There were 246 biochemicals not fully validated that were determined to meet acceptance criteria and have acceptable performance for inter-day precision using the described methods for streamlined performance assessment.

In another example, using an independent set of 44 urine samples, 445 biochemicals met the % fill criterion of being detected in at least 80% of the samples analyzed over multiple days. Performance of all of these biochemicals for inter-day precision was further assessed using CV. In this example, 370 of the 445 biochemicals also had a CV of less than 25% and were determined to meet % CV acceptance criterion and have acceptable performance for inter-day precision; 147 of the 370 represent molecules that were fully analytically validated. There were 223 biochemicals not fully validated that were determined to meet acceptance criteria and have acceptable performance for inter-day precision using the described methods for streamlined performance assessment.

Inter-day precision was determined for biochemicals in CSF samples analyzed by LC-MS as described in the General Methods section above. In one example, using 32 CSF samples, of the biochemicals detected in at least 80% of the samples analyzed over multiple days, 212 biochemicals also had a CV of less than 25%. These biochemicals were determined to meet acceptance criteria and have acceptable performance for inter-day precision; 86 represent molecules that were fully analytically validated. There were 126 biochemicals not fully validated that were determined to meet acceptance criteria and have acceptable performance for inter-day precision using the described methods for streamlined performance assessment.

In another example, using an independent set of 32 CSF samples, of the biochemicals detected in at least 80% of the samples analyzed over multiple days, 210 biochemicals also had a CV of less than 25%. These biochemicals were determined to meet acceptance criteria and have acceptable performance for inter-day precision; 85 represent molecules that were fully analytically validated. There were 125 biochemicals not fully validated that were determined to meet acceptance criteria and have acceptable performance for inter-day precision using the described methods for streamlined performance assessment.

Inter-platform Precision. Two pooled human EDTA plasma samples, referred to as Test Sample 1 (T1) and Test Sample 2 (T2), were used to evaluate precision. Each test sample was created by pooling six (6) different EDTA plasma samples described above (i.e., six healthy adult plasma samples were pooled to create Test Sample 1 and six healthy adult plasma samples, different from the samples used to create Test Sample 1, were pooled to create Test Sample 2). Certain metabolites, designated as rare metabolites, are only seen in diseased patient samples and not in samples from healthy individuals. Since these rare metabolites were absent in Test Sample 1 and 2, they were spiked into these pooled samples to evaluate performance on the platforms. The two test samples were run on all four platforms (Q, R, S and T) with 5 replicates each across 5 days.

To determine the inter-platform (between instrument system) precision, embedded pools of plasma samples collected from healthy volunteers (i.e., normalizing matrix) were included and used to normalize the test samples across five days (days 1-5). Nine sample pools made from aliquots from plasma samples from 26 healthy adult volunteers, approximately half female and half male, were run with each sample batch and alongside the test sample replicates. Inter-platform precision for each compound was evaluated by calculating the % CV of the normalized raw intensity values (i.e., raw ion intensities of each compound/the average raw ion intensities of the compound in the embedded pool samples) for each replicate sample over all five days (i.e., 5 replicates×5 days) and across four independent instrument platforms.

Normalizing matrix samples were used to calculate the inter-assay precision of the technical replicates of 206 (T1)/207 (T2) compounds on Platform R to determine the average % CV's of 8.7% and 11.5% for Test Sample 1 (T1) and Test Sample 2 (T2), respectively. In addition, the precision of 173 (T1)/174 (T2) compounds measured on all five days and across all platforms showed an average inter-platform CV of 10.2% and 11.5%, respectively. Based on these results, the metabolites were determined to meet acceptance criteria and have acceptable performance.

The invention claimed is:

1. A method of assessing the analytical performance of a biochemical measured using a multi-analyte assay, the method comprising:
   a) analytically validating the measurements of the level of a first biochemical in a sample, wherein the first biochemical is analytically validated for three or more analytical validation conditions selected from the group consisting of: Intra-day Precision, Inter-day Precision, Linearity, Limit of Detection/Quantitation, Matrix effect, Exogenous interference, Carryover, Recovery, Stability or Correlation with standard clinical assays;
   b) measuring the level of a second biochemical in a sample, wherein the second biochemical is structurally or biochemically related to the first biochemical;
   c) for the second biochemical, selecting one or more of the three or more analytical validation conditions;
   d) calculating one or more performance value(s) for the selected one or more analytical validation conditions for the second biochemical based on the measured level of the second biochemical;
   e) comparing the calculated one or more performance value(s) for the selected one or more analytical validation conditions for the second biochemical to an acceptance criterion for the three or more analytical validation conditions for the first biochemical; and
   f) determining the analytical performance of the second biochemical to be acceptable if the calculated one or more performance value(s) of the second biochemical meets the acceptance criterion for the three or more analytical validation conditions for the first biochemical; and
   g) determining the analytical performance of the second biochemical to be unacceptable if the calculated one or more performance value(s) of the second biochemical does not meet the acceptance criterion for the three or more analytical validation conditions for the first biochemical.

2. The method of claim 1, wherein the multi-analyte assay comprises mass spectrometry.

3. The method of claim 1, wherein the multi-analyte assay comprises liquid chromatography and mass spectrometry.

4. The method of claim 1, wherein the one or more performance values for the one or more analytical validation conditions are calculated using correlation analysis ($R^2$), % fill, % Systematic Error (SE), % Bias, % Difference, or % Coefficient of Variation (CV).

5. The method of claim 4, wherein one of the one or more analytical validation conditions is selected from the group consisting of intra-day precision or inter-day precision and a performance value of 30% CV or less meets the acceptance criterion.

6. The method of claim 1, wherein two analytical validation conditions are selected for the second biochemical.

7. The method of claim 6, wherein the two analytical validation conditions are intra-day (single day) precision and inter-day (multi-day) precision.

8. A method of assessing the analytical performance of a biochemical measured using a multi-analyte assay, the method comprising:
   a) measuring the level of a biochemical in a sample, wherein the biochemical is structurally or biochemically related to one or more biochemicals that were previously fully analytically validated;
   b) selecting one or more analytical validation conditions from the group comprising single-day precision (intra-day precision), multi-day precision (inter-day precision), limit of detection/quantitation (LOD/LOQ), linearity, stability, carryover, matrix effect, biochemical recovery, interference, or correlation with standard clinical assays;
   c) calculating one or more performance value(s) for the selected one or more analytical validation conditions for the biochemical based on the measured level of the biochemical in the sample;
   d) comparing the calculated one or more performance value(s) for the one or more analytical validation conditions for the biochemical to an acceptance criterion for the one or more analytical validation conditions for the previously validated one or more biochemicals; and
   e) determining the analytical performance of the biochemical to be either acceptable, if it meets the acceptance criterion, or unacceptable, if it does not meet the acceptance criterion, for the corresponding analytical validation condition.

9. The method of claim 8, wherein the multi-analyte assay comprises mass spectrometry.

10. The method of claim 8, wherein the multi-analyte assay comprises liquid chromatography and mass spectrometry.

11. The method of claim 8, wherein the one or more performance values for the one or more analytical validation conditions are calculated using correlation analysis ($R^2$), % fill, % Systematic Error (SE), % Bias, % Difference, or % Coefficient of Variation (CV).

12. The method of claim 11, wherein one of the one or more analytical validation conditions is selected from the group consisting of intra-day precision or inter-day precision and a performance value of 30% CV or less meets the acceptance criterion.

13. The method of claim 8, wherein two analytical validation conditions are selected.

14. The method of claim 13 wherein the two analytical validation conditions are intra-day (single day) precision and inter-day (multi-day) precision.

15. A method of assessing the analytical performance of a biochemical measured using a multi-analyte assay, the method comprising:
   a) analytically validating the measurements of the level of a first biochemical in a sample, wherein the first biochemical is analytically validated for three or more analytical validation conditions selected from the group consisting of:
   Intra-day Precision, Inter-day Precision, Linearity, Limit of Detection, Matrix effect, Exogenous interference, Carryover, or correlation with standard clinical assays;
   b) measuring the level of a second biochemical in a sample, wherein the second biochemical is structurally or biochemically related to the first biochemical;
   c) calculating one or more performance value(s) for one or more of the selected three or more analytical validation conditions for the first biochemical based on the measured level of the first biochemical;
   d) for the second biochemical, calculating one or more performance value(s) for the one or more of the selected three or more analytical validation conditions based on the measured level of the second biochemical;
   e) comparing the calculated one or more performance value(s) for the analytical validation conditions for the first biochemical with the calculated one or more performance value(s) for the analytical validation conditions for the second biochemical;
   f) determining the performance of the second biochemical to be acceptable if the calculated one or more performance value(s) for the second biochemical are within 50% of the calculated one or more performance value(s) for the first biochemical; and
   f) determining the performance of the second biochemical to be unacceptable if the calculated one or more performance value(s) for the second biochemical are not within 50% of the calculated one or more performance value(s) for the first biochemical.

16. The method of claim 15, wherein the one or more performance values for the three or more analytical validation conditions comprise % fill and/or % CV.

17. The method of claim 15, wherein two of the three or more analytical validation conditions are intra-day (single day) precision and inter-day (multi-day) precision.

18. The method of claim 15, wherein the assay comprises mass spectrometry.

19. The method of claim 15, wherein the assay comprises liquid chromatography and mass spectrometry.

* * * * *